United States Patent
Leuenberger

(10) Patent No.: US 6,501,086 B1
(45) Date of Patent: Dec. 31, 2002

(54) METHOD AND DEVICE FOR EVALUATING DEFECTS IN FLAT TEXTILE STRUCTURES

(75) Inventor: Rolf Leuenberger, Hermatswil (CH)

(73) Assignee: Zellweger Luwa (CH)

( * ) Notice: Subject to any disclaimer, the term of this patent is extended or adjusted under 35 U.S.C. 154(b) by 0 days.

(21) Appl. No.: 09/744,446
(22) PCT Filed: Jul. 19, 1999
(86) PCT No.: PCT/CH99/00330
§ 371 (c)(1),
(2), (4) Date: Mar. 8, 2001
(87) PCT Pub. No.: WO00/06823
PCT Pub. Date: Feb. 10, 2000

(30) Foreign Application Priority Data

Jul. 24, 1998 (CH) ............................................. 1562/98

(51) Int. Cl.[7] ............................................. G01N 21/93
(52) U.S. Cl. .................................. 250/559.45; 356/429
(58) Field of Search ....................... 250/559.45, 559.01, 250/559.04, 559.08, 559.2, 559.22, 559.4, 559.41, 559.42, 559.44, 559.46; 356/429, 430

(56) References Cited

U.S. PATENT DOCUMENTS 5,006,722 A * 4/1991 Adelson ................ 250/559.47

FOREIGN PATENT DOCUMENTS

EP 306742 3/1989
GB 2095828a * 10/1982

OTHER PUBLICATIONS

Brzakovic, disigning a defect classification system, Pergamon, Pattern Recognition, Aug. 8, 1995.*
Nickolay, Dr. Bertram and Dr. Harald Schmalfuβ, Automatische Warenschau, Jan. 1993.
Brzakovic and Vujovic, "Designing a Defect Classification System: A Case Study", Pattern Recognition, vol. 29, No. 8, pp. 1401–1419, 1996.

* cited by examiner

Primary Examiner—Robert H. Kim
Assistant Examiner—Hoon K. Song
(74) Attorney, Agent, or Firm—Burns, Doane, Swecker & Mathis, L.L.P.

(57) ABSTRACT

The invention relates to a method and a device for evaluating defects in flat textile structures. To be able to provide a method and a device which permit the repeated and unambiguous evaluation of defects in flat textile structures, the invention provides for an image (1) of a flat structure to be generated such that at least two representations of defects (2–17) in the flat structure appear in the image which differ in terms of the length and contrast of the defect. On the basis of said representations a decision is taken as to whether a defect in the flat structure is admissible or inadmissible. To this end a tabular or matrix-like arrangement of representations of different kinds of defects is created and an image of a defect-free flat surface is used as background.

14 Claims, 5 Drawing Sheets

Figure 1:
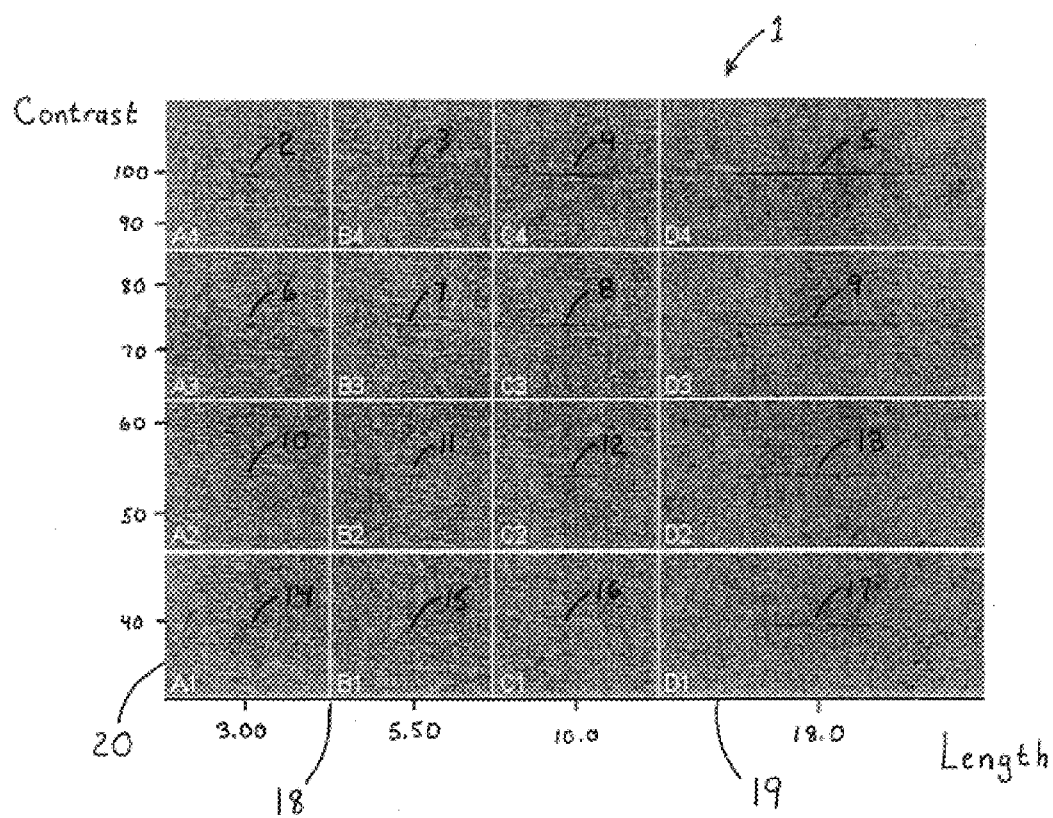

(12) United States Patent
US 6,501,086 B1

METHOD AND DEVICE FOR EVALUATING DEFECTS IN FLAT TEXTILE STRUCTURES

FIELD OF THE INVENTION

The invention relates to a method and a device for evaluating defects in flat textile structures.

BACKGROUND OF THE INVENTION

Hitherto, the procedure for the inspection of fabrics has been, for example, that training of the inspecting personnel in admissible and inadmissible defects in the fabric was based on examples. In the actual inspection, it was then sought to detect defects visually and to assign them to an already known example. Defects which appeared to correspond to examples which were unacceptable were marked as such and others were subsequently ignored, as acceptable defects.

In automatic inspection systems, images of the fabric were subjected to filters which filtered out characteristics of the image, and these were then compared with predefined thresholds. Depending on the result of the comparison, possible defects in the images were marked or simply ignored.

A disadvantage of the first method is the fact that human evaluation of a defect is subjective, and is not always uniformly reproducible. Moreover, the person experiences doubt when there are borderline cases. The latter are then not always treated in the same way. This type of inspection thus results in a non-uniform evaluation of fabric defects. Moreover, this type of evaluation does not always proceed at the same rate. In particular, it is slowed down if the defect at issue is difficult to classify and doubts delay the decision.

In the case of the second method, it is a disadvantage that the above-mentioned comparison with threshold values relate to parameters which do not relate directly to the image or the defect. For example, such a parameter can be a limit frequency which, although it does have a significance for the image, acts in combination with other parameters and, considered in isolation, has an effect on the image which is identifiable only with difficulty and is not always uniform. Such methods have been based particularly on what can be easily automated, but it has had to be accepted that the result is not always definite and does not always serve the desired purpose.

It is evident that speck-type, punctiform or linear defects of comparatively small extent in flat textile structures are perceived in relation to the structure of the surface of such a flat textile structure. Thus, in very homogeneous surfaces, extremely small irregularities are perceived clearly by the eye and appear as disturbing defects. On the other hand, an irregular surface pattern reduces the conspicuousness of small imperfections. A problem consists in finding a valid quantity for the characteristic of the defects which conforms to subjective perception. In particular, an interpretable standard is required for setting the sensitivity on automatic inspection systems.

SUMMARY OF THE INVENTION

The object of the invention, as characterized in the claims, is to create a method and a device which permit the repeated, rapid and unambiguous evaluation of defects in flat textile structures.

This is achieved according to the invention in that, according to the method, an image of a flat structure is generated such that at least two representations of defects in the flat structure are generated which differ in respect of the length and contrast of the defect. On the basis of these representations, a decision is made as to whether a defect in the flat structure is admissible or inadmissible. Particularly advantageous is a tabular or matrix-like arrangement of representations of different kinds of defects, an image of the defect-free flat structure being used as background. The representations of the defects can thus be evaluated in the surrounding which is specific to the task. To this end the image is divided into sections by means of a two-dimensional grid, the length of the defects constituting the first dimension and the contrast of the defects constituting the second dimension. Sensitivity curves are also superimposed on the image.

The advantages achieved by the invention lie particularly in the fact that a method is achieved by which defects in flat textile structures can be evaluated both objectively and by automated means. The method is also suitable for setting the sensitivity of automated inspection systems for flat textile structures. The invention also provides for a device by which automatically and objectively inadmissible defects in flat structures can be separated out without direct human evaluation. According to the invention, it is possible to evaluate defects in a flat structure which result from both the structure and the material used. In the case of a fabric this means that it is possible to evaluate both defects in the alignment of individual weft or warp threads and defects caused by the yarn itself such as, for example, diameter variations.

BRIEF DESCRIPTION OF THE INVENTION

Figure 2:
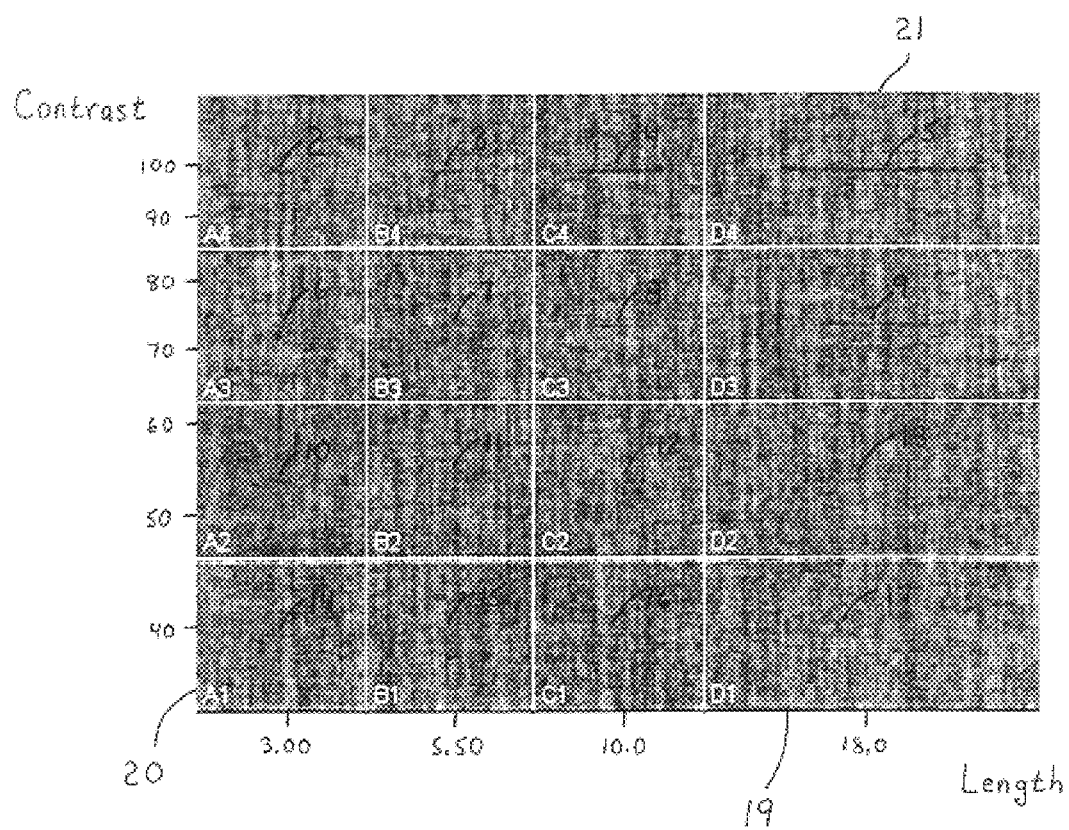
Figure 3:
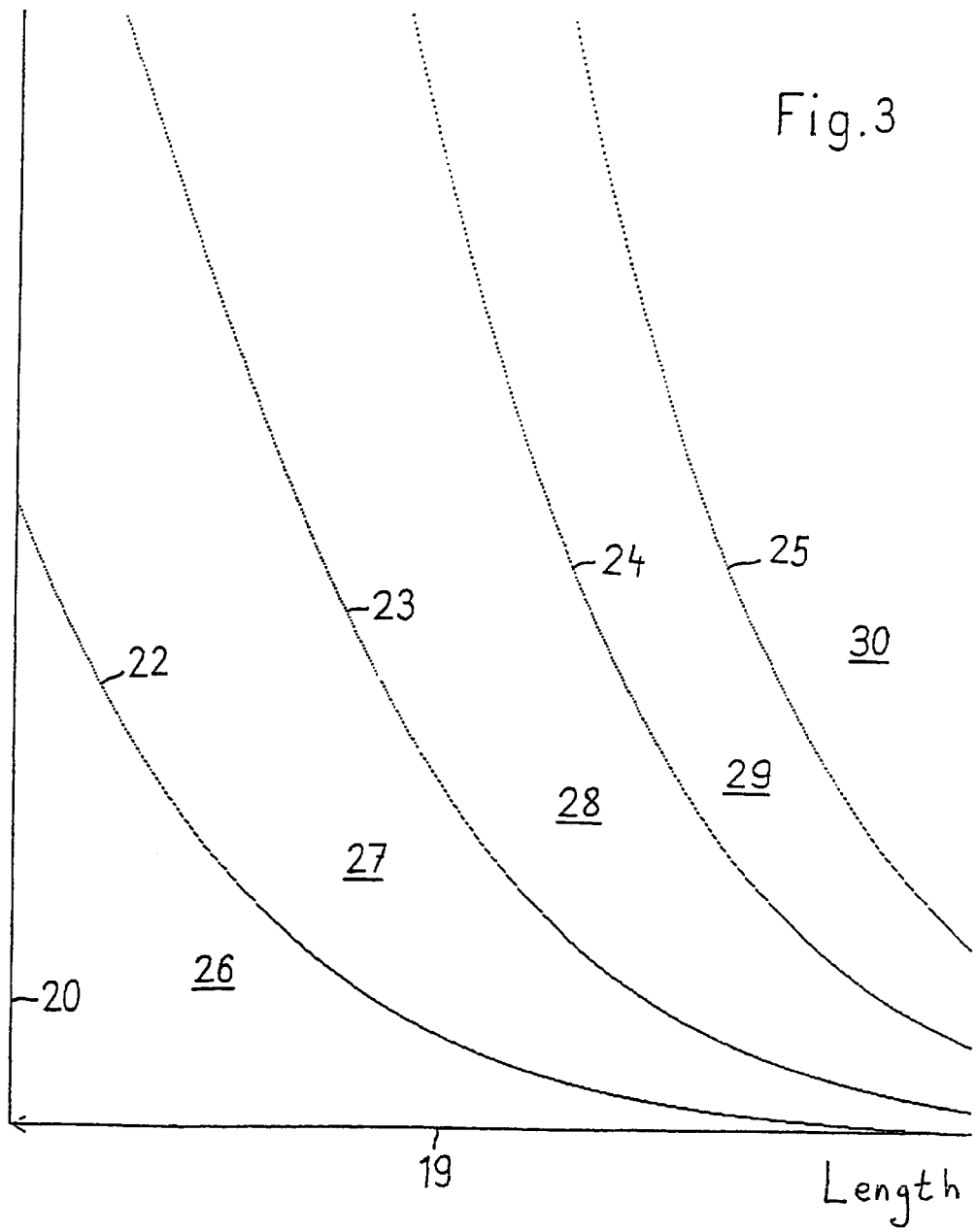
Figure 4:
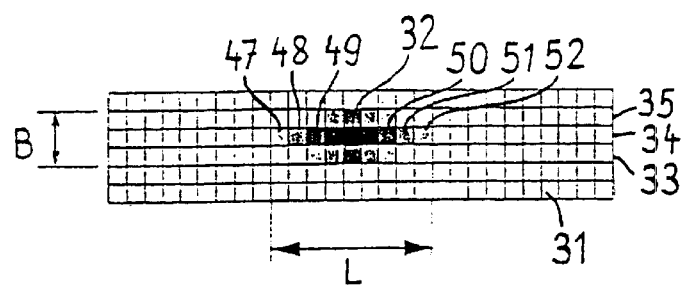
Figure 6:
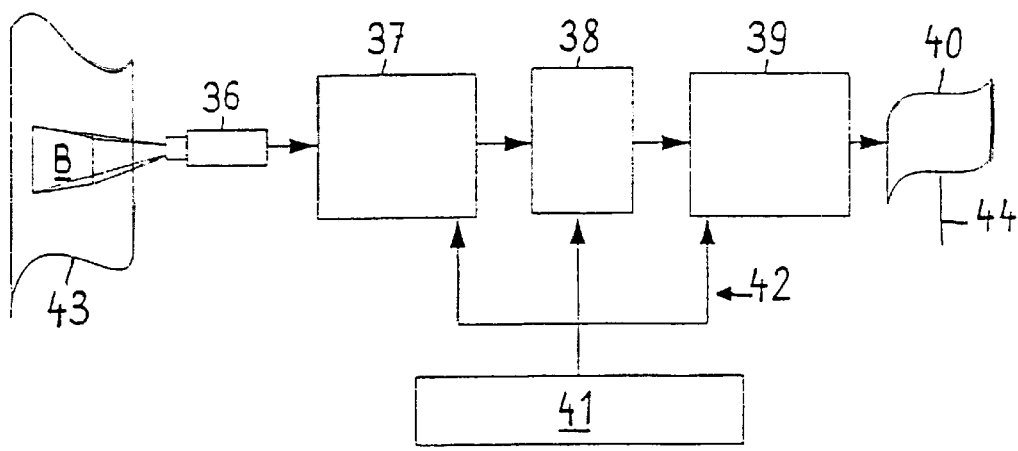
Figure 7:
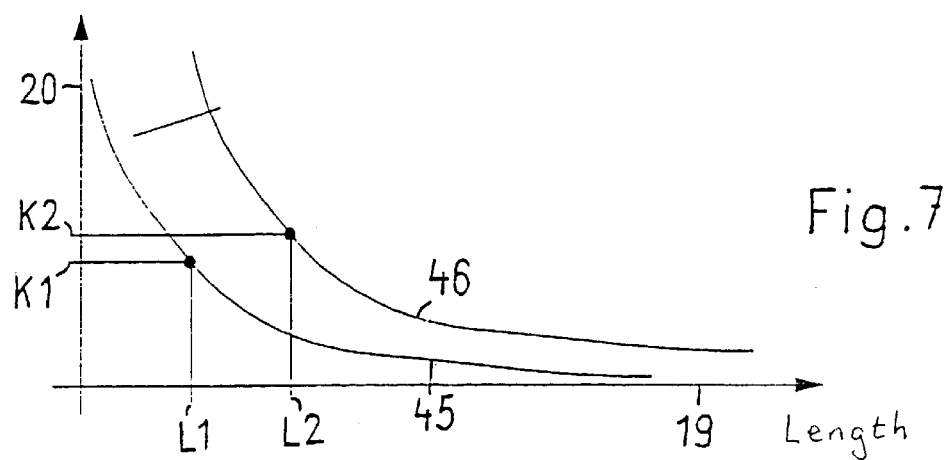
Figure 5:
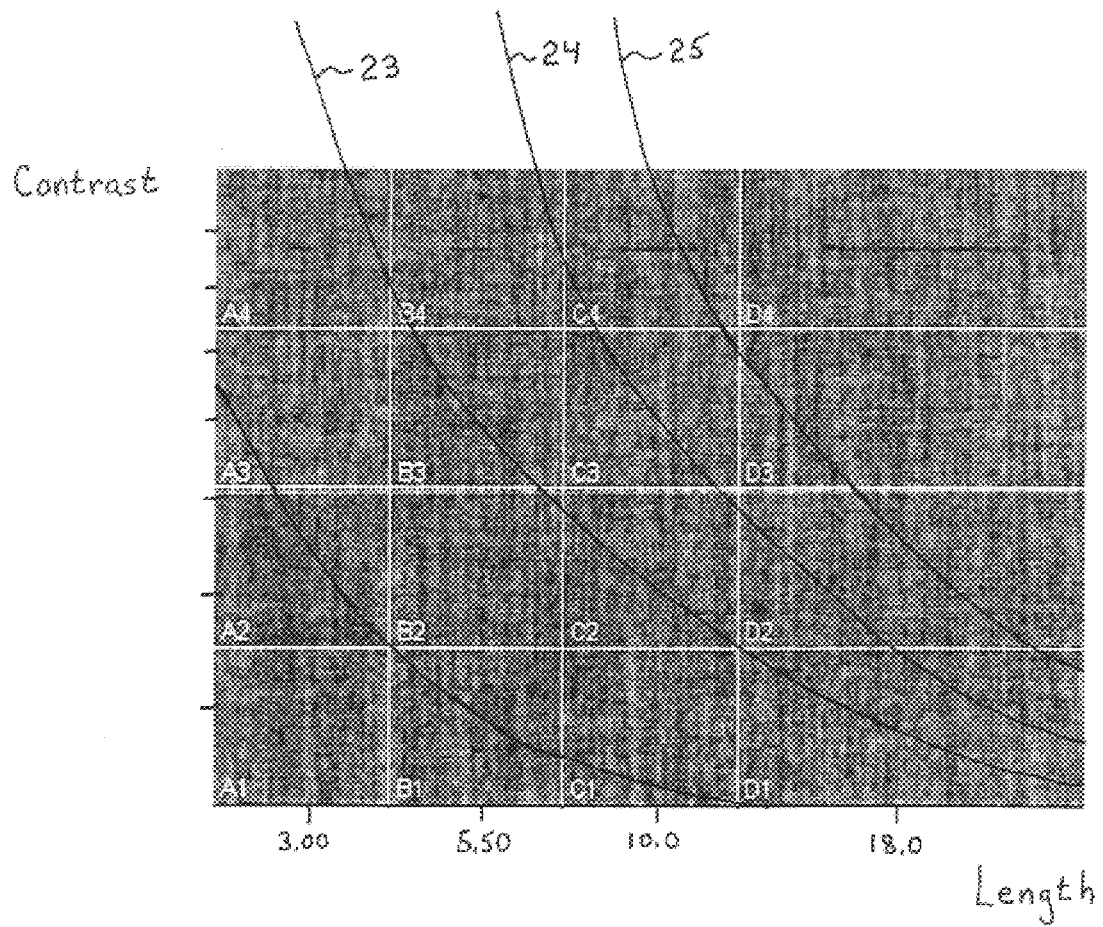

The invention is described more fully below with reference to an example and the accompanying drawings, wherein:

FIG. 1 shows an image of a flat structure with several representations of defects, FIG. 2 shows an image, according to FIG. 1, for another flat structure, FIG. 3 shows a representation of sensitivity curves, FIG. 4 shows an individual representation of a defect, in enlarged scale, FIG. 5 shows a representation of the sensitivity curves on a flat structure, FIG. 6 shows a block diagram for the structure of a device according to the invention, and FIG. 7 shows a representation of characteristics of an inspection device.

DETAILED DESCRIPTION

FIG. 1 shows an image 1 of a flat textile structure such as, for example, a fabric, a fleece, etc., in which several representations 2 to 17 of defects are artificially inserted. These defects differ in respect of length and contrast, which means that each defect has either a length or a contrast level which is peculiar to it. The image 1 is divided into sections A1–A4, B1–B4, C1–C4 and D1–D4 by a two-dimensional grid 18 formed by vertical and horizontal lines and a defect is represented in the centre of each section. Assigned to each section is a length for the represented defect, in this case, for example, by FIGS. 3.00, 5.50, 10.0 and 18.0. These are arranged along a horizontal axis 19: Stated along a vertical axis 20 are values 40–100 for the sensitivity or the quantity of the contrast of the defect in relation to the defect-free background or flat textile structure.

FIG. 2 shows an image 21 which has exactly the same structure as the image 1 and is provided with axes 19, 20 and a grid 18. Also represented therein are exactly the same sections 2–17. The only difference is that it shows a different flat structure, with a comparatively coarse structure as background for the defects.

FIG. 3 shows sensitivity curves 22, 23, 24 and 25, which are drawn over the axes 19, 20 known from FIGS. 1 and 2. In this case, the sensitivity curves 22–25 delimit four levels for the sensitivity of the detection of a defect in the flat structure. The sensitivity curve 22 delimits, between itself and the axes 19 and 20, a region 26 in which there can lie defects of a length and contrast which could still be admissible, even in the case of exacting requirements in respect of the appearance of the flat structure. Located between the sensitivity curves 22 and 23 is a region 27 with a sensitivity which is already reduced in relation to the region 26. Thus, the sensitivity as represented by the regions 28, 29 and 30 between the sensitivity curves 23 and 24 and 24 and 25 or beyond the sensitivity curve 25 is reduced even further, which means that defects which are visible to a greater or lesser extent can be considered to be admissible through a preselection according to one of these sensitivity curves.

FIG. 4 shows a representation of a defect 32 in an image of a flat textile structure. For the purpose of output via means for electronic representation such as, e.g., a monitor or printer, the image of the flat structure is divided into individual image elements which are represented in a section by, for example, a grey-scale value. Such an image element is denoted, for example, by 31. The image elements are aligned in horizontal rows. A defect preferably extends over three adjoining rows such as, in this case, over rows 33, 34 and 35. It can be seen in this case that the image elements become progressively darker towards the centre of the defect 32, or contrast more sharply with the surrounding, which represents the flat structure. This applies as viewed both over the length L and over the width B of the defect 32. Viewed over the width B, however, only two levels are possible if the width is three rows, namely, one level in each case as viewed from each side. In relation to a real defect, the representation of a defect is simulated as accurately as possible in that a transition region is assigned to each defect in this image element representation. In this case, this transition region is formed by the image elements in the rows 33 and 35 and the image elements 47 to 52 in row 34. This representation is based, for example, on the assumption that a row in the image corresponds approximately to a thread or yarn in the fabric. A row, however, can also represent several threads. In this case, an image element represents an averaging of threads and spaces between the threads and, consequently, a two-dimensional averaging of a three-dimensional form.

FIG. 5 shows a representation of an image 1 according to FIG. 1 on which, however, the sensitivity curves according to FIG. 3 are superimposed.

FIG. 6 shows a structure of a device according to the invention. This consists of an image-recording device 36, a first image memory 37, a computing unit 38, a second image memory 39 and an output unit 40, all connected in series. It also comprises an address logic unit 41 for image elements which is connected to the first and the second image memory 37, 39 and to the computing unit 38 via a bus 42. The image-recording device 36 is directed and set to a flat textile structure 43. The output unit 40 preferably has a connection 44 for the input of characteristics to an inspection device for defects in flat textile structures.

FIG. 7 shows characteristics 45, 46, entered over axes 19 and 20 as known from FIGS. 1 and 2, of an automatic device for the inspection of flat textile structures. On this device it is possible to set, for example, the length of a defect and the contrast that is caused in the image by the defect. The characteristics 45, 46 shown represent possible predefinitions for the device with which the device operates and according to which it evaluates defects.

The method according to the invention operates as follows: Firstly, there is generated an image B (FIG. 6) of a flat textile structure, such as, for example, that known from FIG. 1, but without defects or representations of defects. This can be performed by means of the image-recording device 36. This image B is delivered to the first image memory 37 and then stored. This image B can be generated through lighting with incident light, i.e., frontally incident light, or with back lighting, in which case the image-recording device 36 and a light source are disposed on different sides of the flat structure.

In order to produce a basis for an evaluation of real defects in the flat structure 43, representations of typical defects are included in the image B. To this end, the image B is firstly divided into sections A, B, C, D, etc. by a two-dimensional grid 18. One dimension of this grid 18 represents the quantity for the length L of the defects, this being preferably in one direction for continuously increasing length of the defects. The other dimension of the grid in the other direction represents a quantity for increasing contrast K of the defects. One or both dimensions are preferably graduated in a logarithmic scale. Representations of defects, in this case the defects 2–17 for example, are then generated within the image at predefined locations in the grid 18, which are preferably distributed in a uniform manner. Their length and contrast correspond to the location of the representation in the grid 18. The representations of the defects are generated by variation of the brightness values of several image elements of the image B. The brightness progression within a representation in the longitudinal direction of the defect is to be selected according to a function which is to be predefined. A so-called "rised cosine" function can preferably be used. The brightness for each image element is calculated according to the formula $$g'=g-\Delta g \qquad (1)$$

wherein g is the current brightness of a predefined image element.

The brightness variation $\Delta g$ of a given image element is calculated on the basis of the mean brightness value $\bar{g}$ of all image elements in the image, according to the formula $$\Delta g = \bar{g} \cdot K/100 \cdot f(x) \qquad (2)$$

wherein, for f(X), the formula $$f(x)=0.5 \cdot (\cos(x \cdot 2\pi/L)+1) \text{ for } x=(-0.5L \ldots +0.5L) \qquad (3)$$

is applicable.

In the formula, L is a value for the length of the defect and K is a value for the contrast of the defect, in percentages. In the representations of the defects in the flat structure in three rows 33, 34, 35, only the middle row 34 has the full brightness variation. The two outer rows 33 and 35 are modified by a fraction, e.g., half of the brightness variation. If back lighting is used, a defect results in a reduction of the brightness and the value of the brightness variation must be subtracted accordingly from the current value. If incident lighting is used, a defect results in a light/dark transition and the value of the brightness variation for the first two rows 34 and 35 must added accordingly to the current value and, for the third row 33, subtracted from the current value. The image 1 thus obtained, according to FIG. 1, then shows on the flat structure 43 in question, in this case a fabric, sixteen different representations of defects which are arranged according to a system, namely, defects of short length on the left in the image, defects of long length on the right in the image, defects with a sharp contrast at the top of the image and those with a weak contrast at the bottom of the image. It can be seen that defects at the bottom left of the image are less conspicuous than those at the top right of the image. Essentially, the same facts are ascertained if one examines an analogous representation of defects, such as those that can occur in a comparatively coarse-meshed fabric, in FIG. 2. In this case, however, it can be seen that the defects are less conspicuous generally and in some cases cannot be identified at all. This applies particularly to defects at the bottom left of the image. The image 1 is converted into the image according to FIG. 5 by the inclusion of sensitivity curves 22–25, as known from FIG. 3. These sensitivity curves can now be used to specify what is to be acceptable as a defect and what is not to be acceptable. For example, if it is determined, on the basis of examination of the image, that the sensitivity curve 23 determines what is admissible and what is inadmissible, this means that the defects which correspond to the representations 2, 6, 10, 11, 14, 15, 16 can be accepted and the remaining defects cannot be accepted. It is then possible to define, through the single specification of such a sensitivity curve, which defects are admissible for a flat structure. In the simplest case, this is achieved through comparison of a known defect with the representations according to FIG. 5.

In the case of automatic evaluation of defects, the procedure is as follows. The image B stored in the first image memory 37 is copied from the first image memory 37 into the second image memory 39 by means of the address logic unit 41, with the original brightness value of selected image elements being varied in the computing unit 38 in dependence on their position according to image 1 (FIG. 1). The variation of the brightness values is effected in such a way that the image in the second image memory 39 contains representations of typical defects at predefinable points. An image 1 according to FIG. 1 is thus obtained. The output unit 40 then represents the content of the second image memory 39 in an image, with scales being superimposed for axes 19, 20 from which it is possible to read off the length and the contrast of the defects. On the basis of either a visual interpretation or the scale values, limit values can then be determined for an optimum setting for an automatic inspection system which is matched to the natural image of the surface of the textile structure. Such limit values relate, for example, to the length L and the contrast K of admissible defects. The values which are selected thus are entered in this system so that it can then automatically identify and mark defects which must be separated out.

A family of sensitivity curves 22–25, as known from FIG. 3, can also be superimposed on the image 1 of the output unit 40, the parameters of one sensitivity curve selected from amongst them forming the input values for the automatic device. Alternatively, a characteristic originating from the automatic inspection system itself which takes account of the mode of operation of the latter can be superimposed on the image in the output unit 40. Examples of such characteristics are known from FIG. 7 and could thus be superimposed as sensitivity curves according to FIG. 5.

The characteristics of an automatic inspection system are determined by setting variables, such as, for example, filter parameters, limit frequencies and threshold values, of appropriate processing stages within the inspection system. The selection of a particular characteristic as a sensitivity curve thus also determines the associated setting variables.

There is often a multiplicative relationship between individual setting variables (e.g. threshold values) of the inspection system and the defect contrast. In this case, the effect of such setting variables on the progression of the sensitivity curves can be represented by a vertical displacement of the unchanged characteristic if the vertical axis for the defect contrast is scaled logarithmically. The same applies to setting variables which have a multiplicative relationship to the defect length (e.g. limit frequencies). If the horizontal axis for the defect length is scaled logarithmically, the effect of a multiplicative influencing variable on the defect length can be represented through a horizontal displacement of the unchanged characteristic. FIG. 7 shows the characteristic of an automatic inspection system in two positions, which differ through a vertical displacement of a nominal defect contrast K1 to K2 and a horizontal displacement of a nominal defect length L1 to L2. The two displacements have a multiplicative influence on the associated setting variables of the inspection system.

The characteristics are selectable through setting variables such as, for example, defect length L1, L2 and defect contrast K1, K2. If such a value pair is input to the device, for example via the connection 44, this selects a characteristic 45, 46, etc. and the device identifies and marks as defects those defects whose parameters are located to the right of or above the characteristic 45, 46. The device can be a constituent part of an automatic inspection system, the output unit 40 serving simultaneously as a setting element for the sensitivity of the system.

What is claimed is:
1. A method for evaluating defects in flat textile structures, comprising the steps of:
   generating a reference image for the evaluation, by performing the steps of:
      (i) providing an image of a defect-free, flat textile structure, and
      (ii) modifying said image to introduce a plurality of representations of defects that differ from one another in contrast and length; and
   determining the acceptability of a defect in a flat textile structure by reference to said representations in said modified image.
2. The method of claim 1 wherein said representations are presented on said image in a structured arrangement of increasing contrast and increasing length.
3. The method of claim 2 wherein said representations are presented in a two-dimensional array in which the representations increase in contrast along one dimension and increase in length along the other dimension.
4. The method of claim 3 wherein the increase along at least one of said dimensions occurs on a logarithmic scale.
5. The method of claim 1 further including the step of superimposing sensitivity curves on said modified image.
6. The method of claim 1 wherein the modification of the image to introduce said representations is performed by varying brightness values of image elements in said image of the flat textile structure.
7. The method of claim 6 wherein the variation of brightness corresponds to a predefined function.
8. The method of claim 6 wherein the representation of a defect consists of three adjoining rows of image elements in said image.
9. A device for providing a reference image for use in the evaluation of defects in flat textile structures, comprising:
   an image recording device that records an image of a flat textile structure;

a first memory for storing the image recorded by said image-recording device;

a computing unit that processes the image stored in said first memory to vary the brightness value of individual image elements in said image to form a modified image; and a second memory for storing said modified image.

10. The device of claim 9, further including an address logic unit connected to said first and second memories and said computing unit for transferring the image stored in said first memory to said second memory.

11. The device of claim 9 wherein the image stored in said first memory is a defect-free textile structure, and the varied brightness values represent defects in the image stored in said second memory.

12. The device of claim 9 further including an output unit that provides a representation of the contents of the image stored in said second memory.

13. The device of claim 12 wherein said output device provides selection characteristics relating to said image to an automatic inspection device.

14. The device of claim 13 wherein said output device receives selection values and identified defects having parameters that exceed said selection values.

* * * * *